Feb. 7, 1950 H. C. SWIM Plant Pat. 921
ROSE PLANT
Filed Jan. 31, 1949
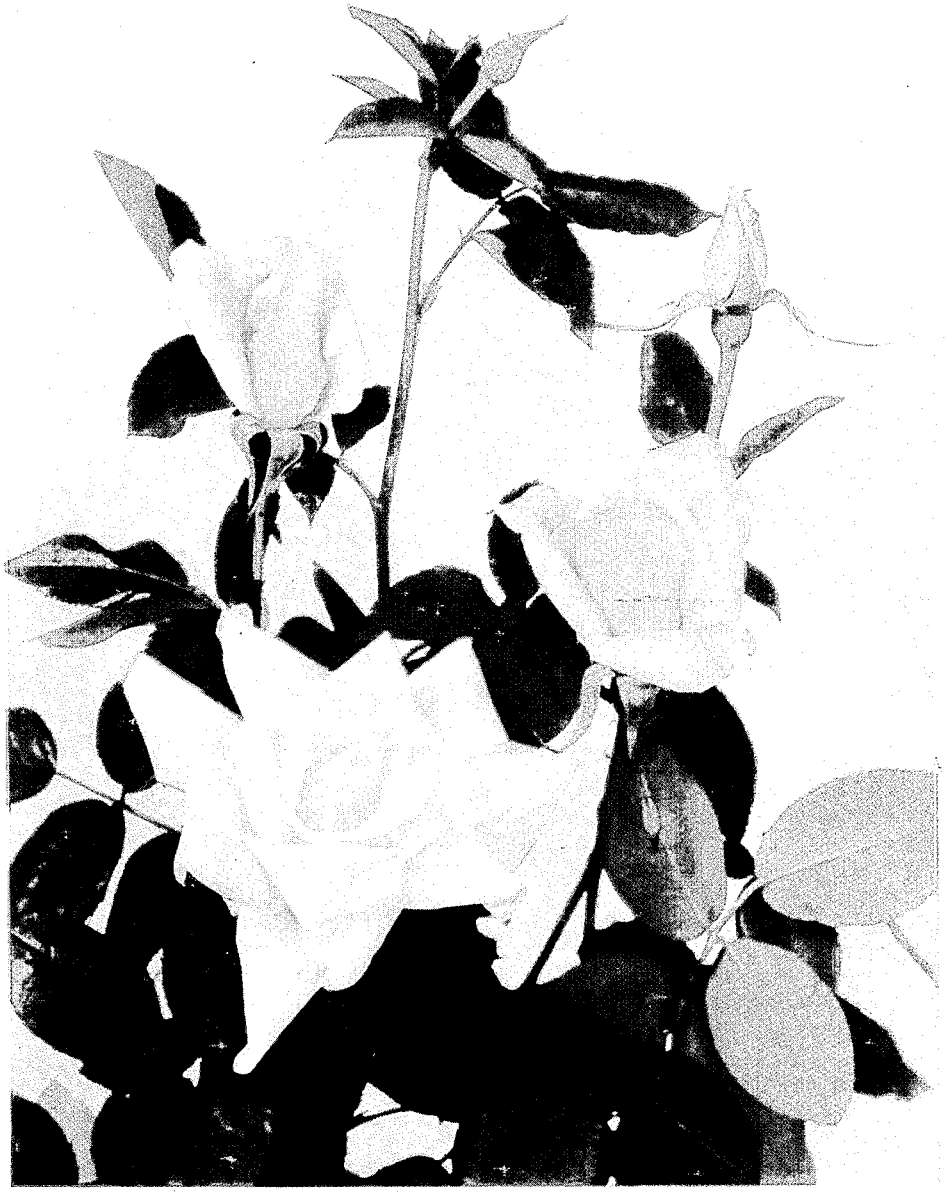
Inventor.
H. C. Swim
By Robert Robb
Attorneys.

Patented Feb. 7, 1950

Plant Pat. 921

UNITED STATES PATENT OFFICE

921

ROSE PLANT

Herbert C. Swim, Ontario, Calif., assignor to Armstrong Nurseries, Inc., Ontario, Calif., a corporation of California Application January 31, 1949, Serial No. 73,761

1 Claim. (Cl. 47—61)

The present invention relates to a new and distinct variety of rose plant having as its object the origination and development of improvements in the parent varieties and similar varieties especially of the hybrid tea class.

This new variety embodies the following combination of distinctive characteristics:

(1) A very free-branching habit resulting in the production of an abundant quantity of flowers.

(2) A combination of bud and flower form with color substantially as described and illustrated herein which is to the best of my knowledge unique and distinct from varieties now available in commerce. The most unusual quality resides in the form of the buds and opening flower. The buds are characterized by a long, slender shape which as they begin to open are characteristically the shape of an urn as a result of the reflexing of the tips of the petals. These buds are further distinctive because of the sharply-drawn points on the apex of each petal.

(3) The qualities mentioned above, combined with a continuous blooming habit make this new variety especially valuable as a rose of the decorative type where color in the garden and cut-flower quality are both desired.

This new variety is distinct from its seed parent, "Charlotte Armstrong," grown under comparable conditions, in the following respects:

(1) A difference of color. This new variety is popularly classed as a light pink, whereas "Charlotte Armstrong" flowers are in varying shades of red.

(2) This new variety has a more sharply-drawn point to the apex of the petals than is characteristic of the petals of "Charlotte Armstrong."

(3) This new variety more closely falls into the decorative class of roses as compared with "Charlotte Armstrong" because of the lighter, more slender, and shorter stems, but with a compensating greater production of flowers.

(4) Whereas the stems of "Charlotte Armstrong" are characterized by many large and many small prickles, the stems of this new variety are not only characterized by relative freedom of large prickles but the complete absence of small prickles.

This new variety is distinct from its pollen parent, "Show Girl," for the following reasons:

(1) Difference of color of bud and flower since this new variety is popularly described as a light pink, whereas "Show Girl" is popularly described as a deep pink.

(2) In type of flower, whereas "Show Girl" frequently produces exhibition-type flowers, this new variety is characteristically of the decorative class with much smaller, more slender buds and smaller open flowers.

(3) This new variety has smaller leaves than "Show Girl," but has the compensating quality of greater abundance of leaves.

(4) This new variety more characteristically produces a single flower to a stem and the stems are of smaller caliper than those characteristic of "Show Girl."

Asexual reproduction of this new variety shows the foregoing characteristics come true to form and are established.

In the accompanying drawings are illustrated specimens of the blooms in the different stages of development from unopen bud to full blown blossoms, and also specimens of young and mature foliage.

The following is a detailed description of this new variety, the color terminology being in accordance with Robert F. Wilson's Horticultural Colour Chart, except where otherwise designated as taken from Ridgway's Color Standards and Nomenclature:

Type: Bush; outdoor; seedling; for cut flowers and garden decoration.

Class: Hybrid tea.

Breeding: Seedling.

*Seed parent.*—"Charlotte Armstrong" (Pl. Pat. #455).

*Pollen parent.*—"Show Girl" (Pl. Pat. #646).

Propagation: Holds its distinguishing characteristics through succeeding propagations by budding.

*Flower*

Locality where grown: Ontario, California.

Flowers borne: Usually singly, sometimes two or more to stem; on normal, medium length stems.

Quantity of bloom: Abundant; outdoors.

Continuity: Continuous during growing season.

Fragrance: Slight; tea.

Bud:

*Peduncle.*—Average length; slender; erect; rough because of numerous gland-tipped cilia and hairs. *Color*—Peacock Green, Plate VI (Ridgway).

*Before calyx breaks.*—*Size*—small. *Form*—short; pointed, with a conspicuous neck; with tomentum on the surface of the bud; usually without foliaceous parts.

*As calyx breaks.*—*Color*—Rose Opal, Plate o22/1, page 110. *Sepals*—inner surface—with tomentum; margins exposed have gland tipped cilia, those covered have tomentum.

*As first petal opens.*—*Size*—average. *Form*—long; pointed to urn-shaped. *Color*—outside: Basal tip of petal is Primrose Yellow, Plate 601/1, page 65, other portions are between Rhodamine Pink, Plate 527/2, page 138, and Dawn Pink, Plate 523/1, page 137, washed in central regions with Rose Madder, Plate 23/2, page 23; inside: Basal tip of petal is Picric Yellow, Plate IV (Ridgway). Central region is Camellia Rose, Plate 622, page 148, shaded toward extremities to Crimson, Plate 22/3, page 22.

*Opening.*—Opens up well. Is not retarded from opening by hot or dry weather.

Bloom: Size, when fully open—average; 2½ inches to 3½ inches.

*Petalage.*—Double; from 20 to 30 petals; plus 2 to 4 petaloids; arranged regularly.

*Form.*—Urn at first; becoming open to cupped; petal margins remaining at first very loosely rolled outward; becoming later, at maturity, somewhat more loosely rolled outward.

Petals:

*Texture.*—Medium thin; with inside satiny and outside shiny to satiny.

*Shape.*—Outside: Broadly obovate with apex pointed. Intermediate: Obovate, mucronate, with apex pointed. Inside: Obovate, mucronate.

*Color.*—Colors may be modified by being overlaid with other colors.

This description of a newly opened flower was made from a rose grown outdoors in the month of September, at Ontario, California:

*Color.*—*Outside petal*—outside surface: Rhodamine Pink, Plate 527/2, page 138, fading to Rhodamine Pink, Plate 527/3, page 138, at petal edges. Basal region of petal is Primrose Yellow, Plate 601/2, page 65; inside surface: Rhodamine Pink, Plate 527/3, page 138. Basal region of petal Primrose Yellow, Plate 601/3, page 65. *Intermediate petal*—outside surface: Dawn Pink, Plate 523/2, page 137, fading to Dawn Pink, Plate 523/3, page 137, at extremities. Base of petal is Primrose Yellow, Plate 601/2, page 65; inside surface: Dawn Pink, Plate 523/3, page 137, with base of petal Primrose Yellow, Plate 601/2, page 65. *Inner petal*—outside surface: Dawn Pink, Plate 523/1, page 137, fading toward edges to Dawn Pink, Plate 523/3, page 137, small basal region of Primrose Yellow, Plate 601/2, page 65; inside surface: French Rose, Plate 520/2, page 136, fading to Shell Pink, Plate 516/3, page 135, at petal edge. Basal area of Primrose Yellow, Plate 601/2, page 65.

This description was made from a rose that was open for three days outdoors in the month of September, at Ontario, California:

*Color.*—*Outside petal*—outside surface: between Rhodamine Pink, Plate 527/3, page 138, and Rhodamine Pink, Plate 527/2, page 138; inside surface: Rhodamine Pink, Plate 527/3, page 138, with shadings of Rhodamine Pink, Plate 527/2, page 138.

*Inside petal*—outside surface: between Rhodamine Pink, Plate 527/3, page 138, and Rhodamine Pink, Plate 527/2, page 138, being near white at petal base; inside surface: Rhodamine Pink, Plate 527/3, page 138, fading toward base to near white.

*General color effect.*—Newly opened flower—French Rose, Plate 520/2, page 136. Three days open—between Rhodamine Pink, Plate 527/3, page 138, and Rhodamine Pink, Plate 527/2, page 138.

*Behavior*—Drop off cleanly except for petaloids; fading to Rose Pink, Plate 427/3, page 126. Not affected by hot or dry weather.

*Flower longevity.*—On bush in garden—3 to 4 days in October. Cut roses grown outdoors kept at living-room temperatures—2 to 3 days in October.

*Reproductive organs*

Stamens: Average number; arranged regularly about pistils.

Filaments: Short to long (8–10 mm.); most with anthers. *Color*—Lemon Yellow, Plate 4/2, page 4.

Anthers: Medium size; open at various times. *Color*—edges: Buttercup Yellow, Plate 5/1, page 5; central portions: Aureolin, Plate 3/3, page 3.

Pollen: Somewhat sparse. *Color*—Indian Yellow, Plate 6/1, page 6.

Pistils: Average number; approximately 45 in number.

Styles: Uneven; average length; loosely bunched. *Color*—Currant Red, Plate 821, page 167, shading into Uranium Green, Plate 63, page 63, in lower ½ to ¾.

Stigma: *Color*—Lemon Yellow, Plate 4/3, page 4, with translucent effect.

Ovaries: Usually all enclosed in calyx.

Hips: Short to average length; near globular; smooth, walls medium thick, fleshy. *Color*—(approximately ¾ mature)—Lime Green, Plate XXXI (Ridgway).

Sepals: Permanent; medium length; reflexed. *Color*—Inside: Parrot Green, Plate VI (Ridgway). Central portion at sepal curve is Pomegranate Purple, Plate XII (Ridgway). Base of sepal is Calliste Green, Plate VI (Ridgway) with whole inside overlaid heavily with a white tomentum; outside: Biscay Green, Plate XVII (Ridgway).

Seeds: Average number; medium size; 12 to 20 in number.

*Plant*

Foliage:

*Leaves.*—Compound of 5 to 7 leaflets; abundant; medium size; moderately heavy, somewhat leathery, semi-glossy.

*Leaflets.*—Shape—ovate, with apex acute; base round; margin doubly serrate.

*Color.*—*Mature*—upper surface: between Spinach Green, Plate o960, page 187, and Parsley Green, Plate oo962/1, page 193; under surface: nearly Lavender Green, Plate ooo761, page 196. *Young*—upper surface: between Cress Green, Plate XXXI (Ridgway), and Light Cress Green, Plate XXXI (Ridgway), with margin overlaid with VanDyke Red, Plate XIII (Ridgway); under surface: Mytho Green, Plate XLI (Ridgway), with veins and margins overlaid with VanDyke Red, Plate XIII (Ridgway).

*Rachis.*—Average size. Upper side—grooved with stipitate glands on edges. Under side—prickly.

*Stipules.*—Medium length; medium width, with medium-length points turning out at an angle of 45° or more.

*Disease.*—More than average resistant to mildew.

Growth:

*Habit.*—Bushy; much branched.

*Growth.*—Free.

*Canes.*—Light to medium caliper.

*Main stems.* — Color — Biscay Green, Plate XVII (Ridgway). *Large prickles*—few; moderately short; hooked slightly downward; with short, narrow base. Color—Cinnamon, Plate XXIX (Ridgway). *Small prickles* — few. Color — Cinnamon, Plate XXIX (Ridgway). Hairs—none.

*Branches.*—Color — Asphodel Green, Plate XLI (Ridgway). *Large prickles* — few; medium length; hooked very slightly downward; with medium-length narrow base. Color—Dresden Yellow, Plate 64/2, page 64, becoming washed with Mahogany Red, Plate II (Ridgway). *Small prickles and hairs*—none.

*New shoots.* — Color — Turtle Green, Plate XXXII (Ridgway). *Large prickles*—few; medium-length; almost straight; hooked slightly downward; with medium-length narrow base. Color—Turtle Green, Plate XXXII (Ridgway) at base; shaded lightly towards the tip with Alizarine Pink, Plate XIII, (Ridgway). *Small prickles*—very few. Color—Turtle Green, Plate XXXII (Ridgway) at base; shaded lightly toward the tip with Alizarine Pink, Plate XIII (Ridgway). *Hairs*—none.

I claim:

A new and distinct variety of rose plant characterized as to novelty by its very free and continuous blooming habits and its abundant quantity of flowers borne singly to a stem; and the unique and distinct form and pink color of the bud and open flowers which make this rose variety particularly adapted for both garden decoration and cut flower purposes, substantially as shown and described.

HERBERT C. SWIM.

No references cited.